US00PP17355P2

(12) United States Plant Patent
Trees

(10) Patent No.: US PP17,355 P2
(45) Date of Patent: Jan. 16, 2007

(54) ***ANTIRRHINUM* PLANT NAMED 'BALUMSUM'**

(50) Latin Name: *Antirrhinum majus*
Varietal Denomination: Balumsum

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 126 days.

(21) Appl. No.: 11/286,812

(22) Filed: Nov. 22, 2005

(51) Int. Cl.
*A01H 5/00* (2006.01)

(52) U.S. Cl. ..... Plt./322

(58) Field of Classification Search ..... Plt./263, Plt./322
See application file for complete search history.

(56) References Cited

PUBLICATIONS

European Plant Breeders' Rights application No. 2006/0508 filed Feb. 20, 2006.

*Primary Examiner*—Kent Bell
*Assistant Examiner*—Annette H Para
(74) *Attorney, Agent, or Firm*—Audrey Charles

(57) ABSTRACT

A new and distinct cultivar of *Antirrhinum* plant named 'Balumsum' characterized by its purple and white bi-colored flowers, medium green-colored foliage, and vigorous, trailing growth habit.

1 Drawing Sheet

Latin name of genus and species of plant claimed: *Antirrhinum majus.*
Variety denomination: 'Balumsum'.

BACKGROUND OF THE INVENTION

The present invention relates to a new and distinct cultivar of *Antirrhinum* plant botanically known as *Antirrhinum majus* and hereinafter referred to by the cultivar name 'Balumsum'.

The new cultivar originated in a controlled breeding program in Arroyo Grande, Calif. during May 2002. The objective of the breeding program was the development of new vigorous *Antirrhinum* cultivars that have numerous flowers with attractive coloration, and freely basal branching, trailing growth habit.

The female (seed) parent of the new cultivar was the proprietary *Antirrhinum majus* breeding selection designated BFP-1525, not patented, characterized by its red and yellow bi-colored flowers, medium green-colored foliage, and semi-trailing growth habit. The male (pollen) parent of the new cultivar was the proprietary *Antirrhinum majus* breeding selection designated BFP-468, not patented, characterized by its lavender-colored flowers, hirsute dark green-colored foliage, and semi-upright growth habit. The new *Antirrhinum* was discovered and selected by the inventor as a single flowering plant within the progeny of the above stated cross-pollination during November 2002 in a controlled environment at Arroyo Grande, Calif.

Asexual reproduction of the new cultivar by terminal stem cuttings since November 2002 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balumsum' as a new and distinct cultivar of *Antirrhinum* plant:

1. Purple and white bi-colored flowers;
2. Medium green-colored foliage; and
3. Vigorous, trailing growth habit.

Plants of the new cultivar differ from plants of the female parent primarily in flower color and growth habit and from plants of the male parent primarily in flower color, foliage color, and growth habit.

Of the many commercially available *Antirrhinum* cultivars known to the inventor, the most similar in comparison to the new cultivar is 'Balumdepur', U.S. Plant Pat. No. 13,097. However, in side by side comparisons, plants of the new cultivar differ from plants of 'Balumdepur' in the following characteristics:

1. Plants of the new cultivar are more compact than plants of 'Balumdepur';
2. Plants of the new cultivar are more floriferous than plants of 'Balumdepur'; and
3. Plants of the new cultivar have a different flower color from plants of 'Balumdepur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balumsum'. The plants were grown in 10 cm pots for 8 weeks in a greenhouse at West Chicago, Ill.

DETAILED BOTANICAL DESCRIPTION

Figure 1:
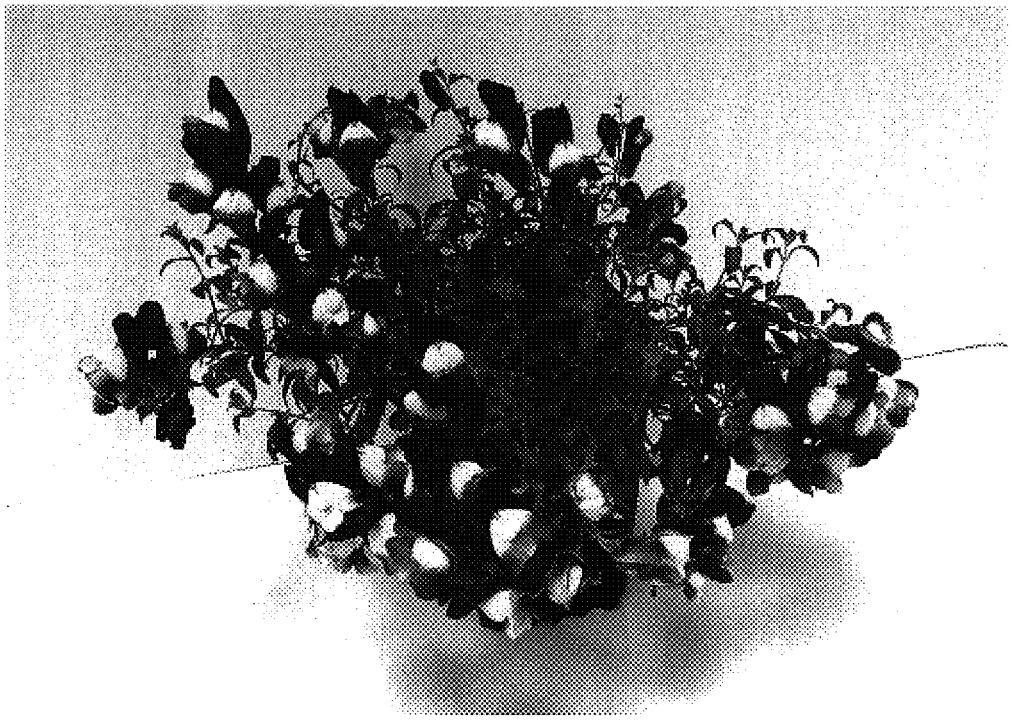
FIG. 1 illustrates a side view of the overall growth and flowering habit of 'Balumsum'.
Figure 2:
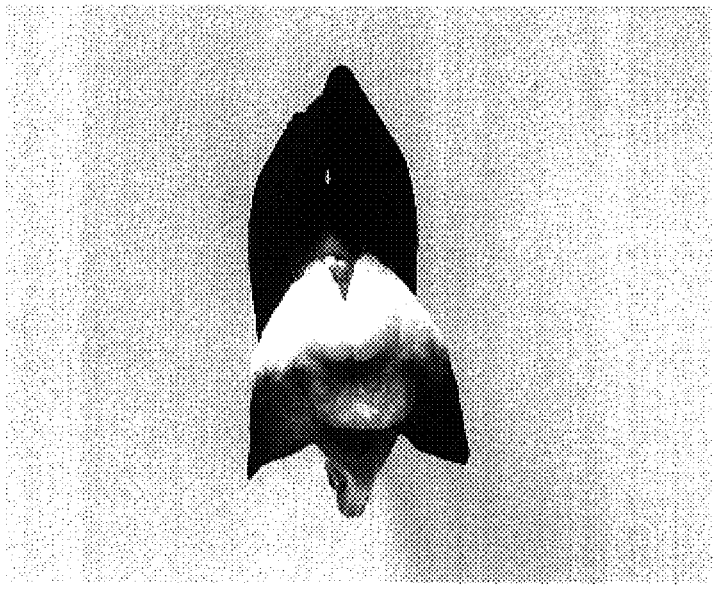
FIG. 2 illustrates a close-up view of an individual flower of 'Balumsum'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 21, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks utilizing a soilless growth medium. Greenhouse temperatures were maintained at approximately 65° F. to 75° F. (18° C. to 24° C.) during the day and approximately 50° F. to 55° F. (10° C. to 13° C.) during the night. Greenhouse light levels of 4,000 to 7,000 footcandles were maintained during the day.

Botanical classification: *Antirrhinum majus* cultivar Balumsum.

Parentage:

*Female parent.*—Proprietary *Antirrhinum majus* breeding selection designated BFP-1525, not patented.

*Male parent.*—Proprietary *Antirrhinum majus* breeding selection designated BFP-468, not patented.

Propagation:

*Type cutting.*—Terminal stem.

*Time to initiate roots.*—Approximately 7 to 12 days.

*Time to produce a rooted cutting.*—Approximately 28 to 35 days.

*Root description.*—Fibrous.

*Rooting habit.*—Freely branching.

Plant description:

*Crop time.*—Approximately 6 to 8 weeks from a rooted cutting.

*Growth habit and general appearance.*—Vigorous, trailing.

*Size.*—Height from soil level to top of plant plane: Approximately 13.2 cm. Width: Approximately 34.7 cm.

*Branching habit.*—Freely basal branching. Approximately 5 main branches per plant with lateral branches potentially forming at every node.

*Branch.*—Strength: Moderate. Shape: Cylindrical. Length: Approximately 12.7 cm. Diameter: Approximately 2.1 mm. Texture: Sparsely pubescent. Color: 144A. Internode length at center of branch: Approximately 2.2 mm.

*Foliage.*—Number of leaves per main branch: Approximately 12. Fragrance: None. Form: Simple. Arrangement: Opposite. Aspect: Perpendicular to stem. Shape: Ovate. Margin: Entire. Apex: Acute. Base: Attenuate. Venation pattern: Pinnate. Length of mature leaf: Approximately 2.8 cm. Width of mature leaf: Approximately 1.2 cm. Texture of upper surface: Puberulent. Texture of lower surface: Glabrous. Color of upper surface of young and mature foliage: Darker than 137A. Color of lower surface of young and mature foliage: 137C. Petiole length: Approximately 5.1 mm. Petiole diameter: Approximately 1.1 mm. Texture of upper surface of petiole: Puberulent. Texture of lower surface of petiole: Glabrous. Color of upper surface of petiole: 143B. Color of lower surface of petiole: 143C.

Flowering description:

*Flowering habit.*—'Balumsum' is freely flowering under outdoor growing conditions with substantially continuous blooming from spring through autumn and year round in greenhouse environment.

*Time to first flower.*—Approximately 11 weeks after sticking of unrooted cutting.

*Lastingness of individual bloom.*—Approximately 9 to 10 days.

Inflorescence description:

*Type.*—Terminal raceme. Number of fully open flowers per raceme at any one time: Approximately 5.

Flower description:

*Type.*—Single, bilabiate. Aspect: Facing outward. Fragrance: None. Length: Approximately 3.6 cm. Width: Approximately 1.7 cm.

*Bud rate of opening.*—Generally takes 3 to 4 days for bud to progress from first color to fully open flower.

*Bud just before opening.*—Shape: Oblong. Length: Approximately 2.1 cm. Diameter: Approximately 8.4 mm. Texture: Densely pubescent. Color: Apex 187C and tube of 70A.

*Corolla.*—Shape: Broadly tubular. Length: Approximately 2.8 cm.

*Upper lobe.*—Lobe shape: Obovate, formed by two fused petals. Lobe width: Approximately 2.7 cm. Petal shape: Obovate. Petal margin: Entire. Texture of upper surface of petal: Glabrous. Texture of lower surface of petal: Moderately pubescent with long hairs. Petal length from throat: Approximately 1.8 cm. Width of each petal: Approximately 1.4 cm. Color of upper surface: Between 71A and N79C. Color of lower surface: 72A with 76A at margin.

*Lower lobe.*—Lobe shape: Ovate to square, formed by three fused petals. Lobe width: Approximately 1.8 cm. Petal shape: Almost square. Petal margin: Entire. Texture of upper surface of central and lateral petals: Glabrous. Texture of lower surface of central petal: Glabrous. Texture of lower surface of lateral petals: Glandular pubescent. Length of central petal: Approximately 6.6 mm. Width of central petal: Approximately 8.8 mm. Length of lateral petals: Approximately 8.4 mm. Width of each lateral petal: Approximately 1.0 cm. Color of upper surface of central petal: N80C. Color of lower surface of central petal: N84D. Color of upper surface of lateral petals: Between 71A and N79C. Color of lower surface of lateral petals: N78C.

*Palate.*—Shape: Ovate, formed by 2 lobes. Texture of inner and outer surfaces: Glabrous. Color of inner and outer surfaces: 155C with 3A at apex of each lobe.

*Corolla tube.*—Length: Approximately 1.5 cm. Diameter: Approximately 1.0 cm. Texture of inner surface of tube: Upper portion and base are glabrous and the lower portion has long matted hairs at opening.

Color of hair: 155C. Texture of outer surface of tube: Densely pubescent. Color of inner surface: N78D with venation 72B. Color of outer surface: N78C with venation 72B.

*Caylx.*—Shape: Star. Width: Approximately 1.2 cm.

*Sepals.*—Quantity per flower: 5, fused at base. Shape: Lanceolate. Apex: Acute. Margin: Entire. Sepal length: Approximately 6.8 mm. Sepal width: Approximately 3.0 mm. Texture of upper and lower surfaces: Densely stipulate-glandular. Color of upper and lower surfaces: 138A. Gland color: Colorless.

*Pedicel.*—Strength: Strong. Aspect: Acute. Length: Approximately 6.4 mm. Diameter: Approximately 1.0 mm. Texture: Densely stipulate-glandular. Color: 138A. Gland color: Colorless.

*Reproductive organs.*—Androecium: Stamen quantity: 4. Stamen length: Two located above stigma are approximately 2.2 cm and two located below stigma are approximately 1.6 cm. Filament color: 155C with overlay of N74D in center. Anther shape: Bilobed. Anther length: Approximately 2.3 mm. Anther color: 13B. Pollen amount: Abundant. Pollen color: 13A. Gynoecium: Pistil quantity: One per flower. Pistil length: Approximately 2.0 cm. Stigma length: Approximately 1.0 mm. Stigma color: N77A. Style length: Approximately 1.6 cm. Style color: 72A. Ovary diameter: Approximately 3.0 mm. Ovary texture: Sericeous. Ovary color: 145A.

Seed and fruit production: Neither seed nor fruit production has been observed.

Disease and pest resistance: Resistance to pathogens and pests common to *Antirrhinum* has not been observed.

What is claimed is:

1. A new and distinct cultivar of *Antirrhinum* plant named 'Balumsum', substantially as herein shown and described.

* * * * *